(12) United States Patent
Suresh et al.

(10) Patent No.: US 12,419,713 B2
(45) Date of Patent: Sep. 23, 2025

(54) SURGICAL INSTRUMENT WITH SENSOR ALIGNED CABLE GUIDE

(71) Applicant: Intuitive Surgical Operations, Inc., Sunnyvale, CA (US)

(72) Inventors: Ashwinram Suresh, San Jose, CA (US); Grant M. Kadokura, San Diego, CA (US); Andrew C. Waterbury, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1001 days.

(21) Appl. No.: 17/293,020

(22) PCT Filed: Nov. 15, 2019

(86) PCT No.: PCT/US2019/061880
§ 371 (c)(1),
(2) Date: May 11, 2021

(87) PCT Pub. No.: WO2020/102774
PCT Pub. Date: May 22, 2020

(65) Prior Publication Data
US 2021/0401523 A1 Dec. 30, 2021

Related U.S. Application Data

(60) Provisional application No. 62/767,880, filed on Nov. 15, 2018.

(51) Int. Cl.
*A61B 34/00* (2016.01)
*A61B 17/00* (2006.01)
(Continued)

(52) U.S. Cl.
CPC .............. *A61B 34/71* (2016.02); *A61B 17/00* (2013.01); *A61B 34/35* (2016.02); *A61B 90/06* (2016.02);
(Continued)

(58) Field of Classification Search
None
See application file for complete search history.

(56) References Cited

U.S. PATENT DOCUMENTS 4,299,230 A 11/1981 Kubota
4,430,895 A 2/1984 Colton
(Continued)

FOREIGN PATENT DOCUMENTS

CN 2772442 Y 4/2006
CN 101721246 A 6/2010
(Continued)

OTHER PUBLICATIONS

International Search Report and Written Opinion for Application No. PCT/US2019/061880, mailed on Mar. 16, 2020, 15 pages.
(Continued)

*Primary Examiner* — Benjamin J Klein
*Assistant Examiner* — Willow Grace Welch

(57) ABSTRACT

Control cables in a surgical instrument are kept parallel to the instrument's longitudinal axis to prevent transverse forces from the cables being sensed by a transverse force sensor in the instrument. A surgical instrument includes an elongated hollow shaft having a longitudinal center axis. Multiple cables extend within the shaft. A force sensor includes a beam disposed within the shaft and one or more strain gauges disposed on the beam. A proximal anchor is disposed within the shaft and in contact with a proximal end of the beam. A distal anchor is at the distal end of the shaft and in contact with a distal end of the beam. A cable guide
(Continued)

is disposed within the shaft to constrain portions of the multiple cables disposed alongside the beam to movement parallel to the center axis, and so prevent force from the moving cables causing transverse force on the beam.

24 Claims, 10 Drawing Sheets

(51) Int. Cl.
*A61B 34/30* (2016.01)
*A61B 34/35* (2016.01)
*A61B 90/00* (2016.01)

(52) U.S. Cl.
CPC .............. *A61B 2017/00477* (2013.01); *A61B 2034/302* (2016.02); *A61B 2034/305* (2016.02); *A61B 2090/064* (2016.02)

(56) References Cited

U.S. PATENT DOCUMENTS

| | | |
|---|---|---|
| 4,799,752 A | 1/1989 | Carome |
| 5,599,348 A | 2/1997 | Gentelia et al. |
| 5,723,826 A | 3/1998 | Kitagawa et al. |
| 5,784,542 A | 7/1998 | Ohm et al. |
| 5,792,135 A | 8/1998 | Madhani et al. |
| 5,855,583 A | 1/1999 | Wang et al. |
| 5,892,860 A | 4/1999 | Maron et al. |
| 6,197,017 B1 | 3/2001 | Brock et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,459,926 B1 | 10/2002 | Nowlin et al. |
| 6,494,882 B1 | 12/2002 | Lebouitz et al. |
| 6,594,552 B1 | 7/2003 | Nowlin et al. |
| 6,620,174 B2 | 9/2003 | Jensen et al. |
| 6,730,021 B2 | 5/2004 | Vassiliades, Jr. et al. |
| 6,817,974 B2 | 11/2004 | Cooper et al. |
| 6,994,708 B2 | 2/2006 | Manzo |
| 7,077,842 B1 | 7/2006 | Cosman et al. |
| 7,083,571 B2 | 8/2006 | Wang et al. |
| 7,169,141 B2 | 1/2007 | Brock et al. |
| 7,320,700 B2* | 1/2008 | Cooper ................ A61B 17/062 |
| | | 600/101 |
| 7,752,920 B2 | 7/2010 | Blumenkranz et al. |
| 7,935,130 B2 | 5/2011 | Williams |
| 8,016,818 B2 | 9/2011 | Ellis et al. |
| 8,365,633 B2 | 2/2013 | Simaan et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,551,115 B2 | 10/2013 | Steger et al. |
| 8,602,288 B2 | 12/2013 | Shelton, IV et al. |
| 8,620,473 B2 | 12/2013 | Diolaiti et al. |
| 8,628,518 B2 | 1/2014 | Blumenkranz et al. |
| 8,771,270 B2 | 7/2014 | Burbank |
| 8,800,838 B2 | 8/2014 | Shelton, IV |
| 8,840,628 B2 | 9/2014 | Green et al. |
| 8,887,595 B2 | 11/2014 | Williams et al. |
| 8,918,212 B2 | 12/2014 | Larkin et al. |
| 8,945,095 B2 | 2/2015 | Blumenkranz et al. |
| 9,028,494 B2 | 5/2015 | Shelton, IV et al. |
| 9,078,684 B2 | 7/2015 | Williams |
| 9,204,923 B2 | 12/2015 | Manzo et al. |
| 9,232,979 B2 | 1/2016 | Parihar et al. |
| 9,707,684 B2 | 7/2017 | Ruiz et al. |
| 9,782,214 B2 | 10/2017 | Houser et al. |
| 9,817,019 B2 | 11/2017 | Blumenkranz et al. |
| 9,952,107 B2 | 4/2018 | Blumenkranz et al. |
| 10,085,809 B2 | 10/2018 | Blumenkranz et al. |
| 10,130,366 B2 | 11/2018 | Shelton, IV et al. |
| 10,201,365 B2 | 2/2019 | Boudreaux et al. |
| 10,219,874 B2 | 3/2019 | Yu et al. |
| 10,238,458 B2 | 3/2019 | Verner et al. |
| 10,285,763 B2 | 5/2019 | Vale et al. |
| 10,365,295 B2 | 7/2019 | Blumenkranz et al. |
| 10,378,883 B2 | 8/2019 | Gifford et al. |
| 10,398,433 B2 | 9/2019 | Boudreaux et al. |
| 10,470,796 B2 | 11/2019 | Page et al. |
| 10,524,870 B2 | 1/2020 | Saraliev et al. |
| 10,653,435 B2 | 5/2020 | Shelton, IV et al. |
| 10,682,141 B2 | 6/2020 | Moore et al. |
| 10,791,908 B2 | 10/2020 | Au |
| 10,881,280 B2 | 1/2021 | Baez, Jr. |
| 11,000,345 B2 | 5/2021 | Lambrecht et al. |
| 11,137,414 B2 | 10/2021 | Blumenkranz et al. |
| 2003/0045834 A1 | 3/2003 | Wing et al. |
| 2006/0235314 A1 | 10/2006 | Migliuolo et al. |
| 2007/0005002 A1 | 1/2007 | Millman et al. |
| 2007/0043338 A1 | 2/2007 | Moll et al. |
| 2007/0052496 A1 | 3/2007 | Niemeyer et al. |
| 2007/0078484 A1 | 4/2007 | Talarico et al. |
| 2007/0119274 A1 | 5/2007 | Devengenzo et al. |
| 2007/0137371 A1 | 6/2007 | Devengenzo et al. |
| 2007/0156019 A1 | 7/2007 | Larkin et al. |
| 2007/0282358 A1 | 12/2007 | Remiszewski et al. |
| 2008/0009838 A1 | 1/2008 | Schena et al. |
| 2008/0046122 A1 | 2/2008 | Manzo et al. |
| 2008/0065105 A1 | 3/2008 | Larkin et al. |
| 2008/0065111 A1 | 3/2008 | Blumenkranz et al. |
| 2008/0087871 A1 | 4/2008 | Schena et al. |
| 2008/0132893 A1 | 6/2008 | D'Amelio et al. |
| 2008/0287963 A1* | 11/2008 | Rogers .................. A61B 1/008 |
| | | 606/130 |
| 2009/0021752 A1 | 1/2009 | Cohen et al. |
| 2009/0088774 A1 | 4/2009 | Swarup et al. |
| 2009/0088775 A1* | 4/2009 | Swarup .................. A61B 34/71 |
| | | 700/264 |
| 2010/0036384 A1 | 2/2010 | Gorek et al. |
| 2010/0063478 A1 | 3/2010 | Selkee |
| 2010/0087835 A1 | 4/2010 | Blumenkranz et al. |
| 2010/0154578 A1* | 6/2010 | Duval .................... A61B 34/30 |
| | | 74/479.01 |
| 2010/0210975 A1 | 8/2010 | Anthony, III et al. |
| 2010/0219388 A1 | 9/2010 | Schena |
| 2010/0298844 A1 | 11/2010 | Blumenkranz |
| 2010/0313679 A1* | 12/2010 | Larkin .................... A61B 34/71 |
| | | 73/862.045 |
| 2011/0071543 A1 | 3/2011 | Prisco et al. |
| 2011/0178477 A1 | 7/2011 | Morel et al. |
| 2011/0230906 A1 | 9/2011 | Modesitt et al. |
| 2011/0277775 A1 | 11/2011 | Holop et al. |
| 2011/0282356 A1 | 11/2011 | Solomon et al. |
| 2011/0295269 A1 | 12/2011 | Swensgard et al. |
| 2011/0295270 A1 | 12/2011 | Giordano et al. |
| 2012/0016362 A1 | 1/2012 | Heinrich et al. |
| 2012/0123441 A1 | 5/2012 | Au et al. |
| 2012/0199632 A1 | 8/2012 | Spivey et al. |
| 2012/0257208 A1 | 10/2012 | Andersen et al. |
| 2012/0310257 A1 | 12/2012 | Kuchenbecker et al. |
| 2013/0291654 A1* | 11/2013 | Blumenkranz ......... G01L 1/246 |
| | | 73/862.045 |
| 2014/0005662 A1 | 1/2014 | Shelton, IV |
| 2014/0005678 A1 | 1/2014 | Shelton, IV et al. |
| 2014/0005681 A1* | 1/2014 | Gee ...................... A61F 9/00745 |
| | | 606/130 |
| 2014/0005708 A1 | 1/2014 | Shelton, IV |
| 2014/0128885 A1 | 5/2014 | Dachs, II et al. |
| 2014/0137667 A1 | 5/2014 | Blumenkranz et al. |
| 2014/0148729 A1 | 5/2014 | Schmitz et al. |
| 2014/0257333 A1 | 9/2014 | Blumenkranz |
| 2015/0150635 A1 | 6/2015 | Kilroy et al. |
| 2015/0374447 A1 | 12/2015 | Blumenkranz et al. |
| 2016/0216167 A1 | 7/2016 | Blumenkranz et al. |
| 2016/0346513 A1 | 12/2016 | Swaney et al. |
| 2017/0007345 A1 | 1/2017 | Smith et al. |
| 2017/0071688 A1 | 3/2017 | Cohen et al. |
| 2017/0095234 A1 | 4/2017 | Prisco et al. |
| 2017/0165017 A1 | 6/2017 | Chaplin et al. |
| 2017/0172687 A1 | 6/2017 | Smith et al. |
| 2017/0215944 A1 | 8/2017 | Keffeler |
| 2017/0265980 A1 | 9/2017 | Borazjani et al. |
| 2018/0042689 A1 | 2/2018 | Mozdzierz et al. |

(56) References Cited

U.S. PATENT DOCUMENTS

| | | | |
|---|---|---|---|
| 2018/0078249 A1 | 3/2018 | Stoy et al. | |
| 2018/0092703 A1 | 4/2018 | Rodriguez-Navarro et al. | |
| 2018/0104011 A1* | 4/2018 | Kadokura | A61B 17/00234 |
| 2019/0069966 A1 | 3/2019 | Petersen et al. | |
| 2019/0094084 A1 | 3/2019 | Swinehart et al. | |
| 2019/0125354 A1 | 5/2019 | Deck et al. | |
| 2019/0175188 A1 | 6/2019 | PV R | |
| 2019/0201018 A1 | 7/2019 | Shelton, IV et al. | |
| 2019/0223960 A1 | 7/2019 | Chaplin et al. | |
| 2019/0231464 A1 | 8/2019 | Wixey et al. | |
| 2019/0336228 A1 | 11/2019 | Blumenkranz et al. | |
| 2020/0046404 A1 | 2/2020 | Page et al. | |
| 2020/0278265 A1 | 9/2020 | Suresh | |
| 2020/0345435 A1 | 11/2020 | Traina | |
| 2021/0045819 A1 | 2/2021 | Castillo et al. | |
| 2021/0196268 A1 | 7/2021 | Shelton, IV et al. | |
| 2021/0310885 A1 | 10/2021 | Dyer et al. | |
| 2021/0353373 A1 | 11/2021 | Ye et al. | |
| 2021/0387337 A1 | 12/2021 | Langenfeld et al. | |
| 2023/0225817 A1 | 7/2023 | Ye et al. | |
| 2024/0130812 A1 | 4/2024 | Suresh | |

FOREIGN PATENT DOCUMENTS

| | | |
|---|---|---|
| CN | 102166136 A | 8/2011 |
| CN | 202105024 U | 1/2012 |
| CN | 102697559 A | 10/2012 |
| EP | 0624346 A2 | 11/1994 |
| EP | 1704822 A1 | 9/2006 |
| EP | 2362285 A2 | 8/2011 |
| EP | 2431000 A2 | 3/2012 |
| EP | 2736680 A2 | 6/2014 |
| EP | 3549538 A1 | 10/2019 |
| JP | 2007528238 A | 10/2007 |
| KR | 20070037565 A | 4/2007 |
| KR | 100778387 B1 | 11/2007 |
| KR | 20140079470 A | 6/2014 |
| WO | WO-9729690 A1 | 8/1997 |
| WO | WO-2007111737 A2 | 10/2007 |
| WO | WO-2007143859 A1 | 12/2007 |
| WO | WO-2012166806 A1 | 12/2012 |
| WO | WO-2016018815 A1 | 2/2016 |
| WO | WO-2017064303 A1 | 4/2017 |
| WO | WO-2017136332 A1 | 8/2017 |
| WO | WO-2018049217 A1 | 3/2018 |
| WO | WO-2019099562 A1 | 5/2019 |
| WO | WO-2020102774 A1 | 5/2020 |
| WO | WO-2020102776 A1 | 5/2020 |
| WO | WO-2020102778 A1 | 5/2020 |
| WO | WO-2020102780 A1 | 5/2020 |
| WO | WO-2021055276 A1 | 3/2021 |
| WO | WO-2021076765 A1 | 4/2021 |
| WO | WO-2021236505 A1 | 11/2021 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Office Action for Chinese Application No. CN201980075392.9, mailed Nov. 18, 2023, 18 pages.

Office Action for CN Application No. 201980075392, mailed Jul. 27, 2024, 15 Pages.

Office Action for CN Application No. 201980075392, mailed Nov. 7, 2024, 10 Pages.

* cited by examiner

SURGICAL INSTRUMENT WITH SENSOR ALIGNED CABLE GUIDE

CLAIM OF PRIORITY

This application is a U.S. national stage filing under 35 U.S.C. § 371 of International Application No. PCT/US2019/061880, entitled "SURGICAL INSTRUMENT WITH SENSOR ALIGNED CABLE GUIDE," filed Nov. 15, 2019, which claims the benefit of priority to U.S. Provisional Patent Application Ser. No. 62/767,880, entitled "SURGICAL INSTRUMENT WITH SENSOR ALIGNED CABLE GUIDE," filed Nov. 15, 2018, each of the disclosures of which is incorporated by reference herein in its entirety.

BACKGROUND

Minimally invasive medical techniques are intended to reduce the amount of tissue that is damaged during diagnostic or surgical procedures, thereby reducing patient recovery time, discomfort, and deleterious side effects. Teleoperated surgical systems that use robot assisted technology may be used to overcome limitations of manual laparoscopic and open surgery. Advances in telepresence systems provide surgeons views inside a patient's body, an increased number of degrees of motion of surgical instruments, and the ability for surgical collaboration over long distances.

In manual minimally invasive surgery, surgeons feel the interaction of the instrument with the patient via a long shaft, which eliminates tactile cues and masks force cues. In teleoperation surgery systems, natural force feedback is eliminated because the surgeon no longer manipulates the instrument directly. Rather, an end effector at a distal end of a long shaft is actuated by control cables that extend within the shaft.

A force sensor within the shaft may be used to measure clinical forces at the distal end of an instrument during a medical procedure due to interaction between an end effector and patient tissue, suture material, etc. But, errors may be introduced to clinical force measurements due to extraneous forces imparted by end effector control cables extending within the shaft. Such extraneous forces may be due to twisting of the cables as the shaft rolls around its longitudinal axis, for example. Thus, there is a need to isolate clinical threes from extraneous mechanical control cable forces so that the clinical forces can be accurately measured.

SUMMARY

In one aspect, a surgical instrument is provided that includes an elongated hollow shaft comprising a proximal end portion, a distal end portion, and a longitudinal shaft center axis extending between the proximal and distal end portions. A force sensor is located within the distal portion of the shaft and coaxial with the shaft center axis. The force sensor comprises a beam and one or more strain gauges on the beam. The beam comprises a proximal end and a distal end. A proximal anchor is located within the shaft and is coupled to the proximal end of the beam. The proximal anchor comprises a first plurality of cable guide holes. A distal anchor is located within the shaft and is coupled to the distal end of the beam. The distal anchor comprises a second plurality of cable guide holes longitudinally aligned with the first plurality of cable guide holes. A plurality of cables extend through the shaft, through the first plurality of cable guide holes, and through the second plurality of cable guide holes. The plurality of cables are constrained to remain parallel to the shaft center axis by the first and second plurality of cable guide holes as the shaft rolls around the shaft center axis.

In another aspect, a surgical instrument is provided that includes an elongated hollow shaft having a longitudinal center axis and including an inner wall defining a center bore. Multiple cables extend within the center bore. A force sensor includes a beam within the center bore and includes one or more strain gauges on the beam. A proximal anchor is within the center bore in contact with an inner wall of the shaft and in contact with a proximal end portion of the beam. A distal anchor is within the center bore and in contact with a distal end portion of the beam. A cable guide is within the center bore to constrain portions of the multiple cables alongside the beam to movement parallel to the center axis.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DESCRIPTION OF EMBODIMENTS

Teleoperated Surgical System

Figure 1:
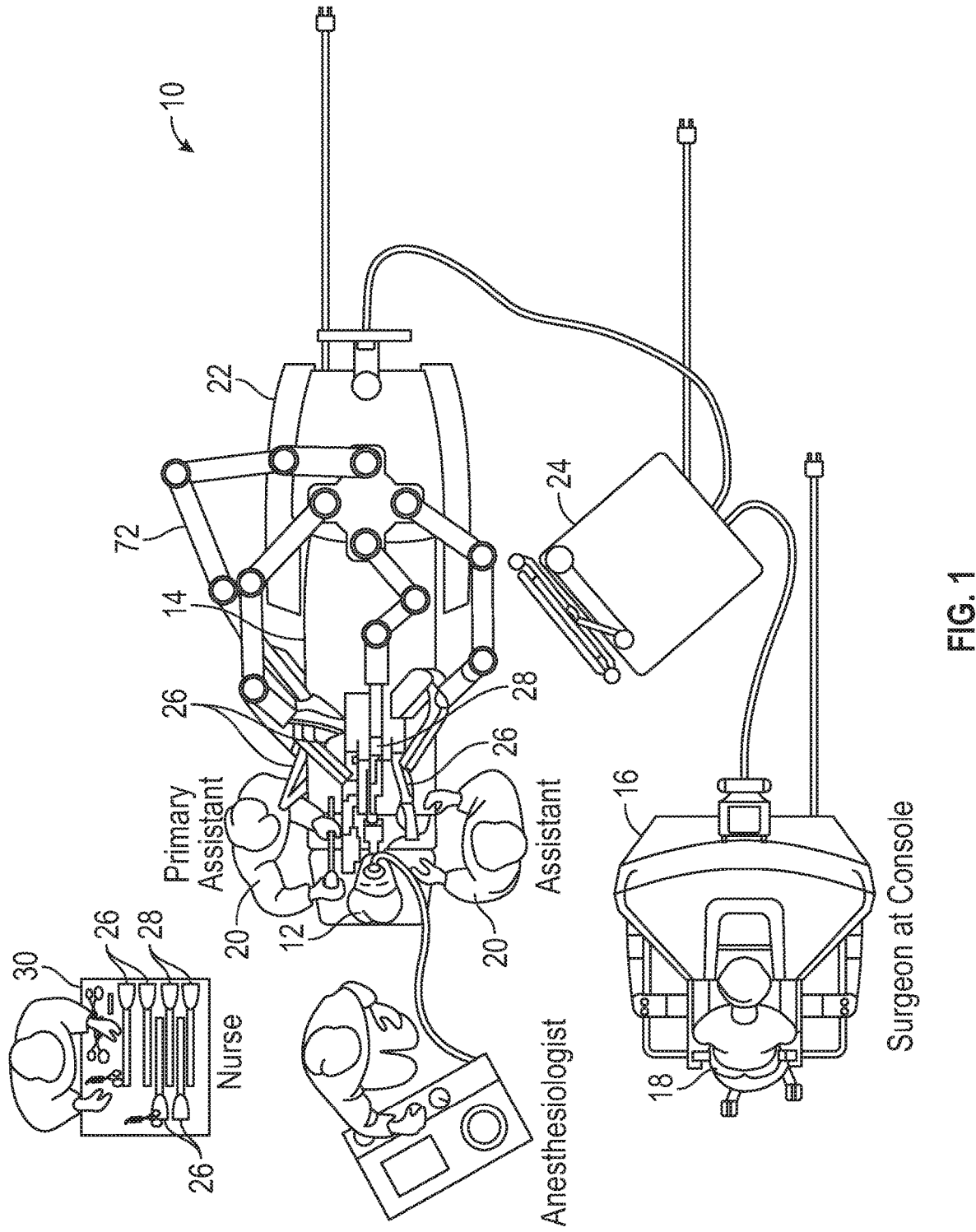
FIG. 1 is an illustrative plan view of a minimally invasive teleoperated surgical system for performing a minimally invasive diagnostic or surgical procedure on a patient who is lying on an operating table.

FIG. 1 is an illustrative plan view of a minimally invasive teleoperated surgical system 10 for performing a minimally invasive diagnostic or therapeutic surgical procedure on a patient 12 who is lying on an operating table 14. The system includes a user control unit 16 for use by a surgeon 18 during the procedure. One or more assistants 20 also may participate in the procedure. The minimally invasive teleoperated surgical system 10 further includes one or more manipulator units 22 and an auxiliary unit 24. The manipulator units 22 can manipulate at least one surgical instrument 26 through a minimally invasive incision in the body or a natural body orifice of the patient 12 while the surgeon 18 views the surgical site through the user console 16. An image of the surgical site can be obtained by an endoscope 28, such as a stereoscopic endoscope, which may be positioned using a manipulator unit 22. Computer processors located on the auxiliary unit 24 may be used to process the images of the surgical site for subsequent display to the surgeon 18 through the user console 16. The computer processor can include a logic unit and a memory that stores instructions carried out by the logic unit. In some embodiments, stereoscopic images may be captured, which allow the perception of depth during a surgical procedure. The number of surgical instruments 26 used at one time will generally depend on the diagnostic or therapeutic procedure and the space constraints within the operative site, among other factors. If it is necessary to change one or more of the surgical instruments 26 being used during a procedure, an assistant 20 may remove the surgical instrument 26 from a manipulator unit 22, and replace it with another surgical instrument 26 from a tray 30 in the operating room. An example computer processor at the auxiliary unit 24 can be configured process signals indicative of forces imparted at the surgical instrument. An example computer processor can produce haptic feedback corresponding to these imparted forces at the surgeon's console 16.

Figure 2:
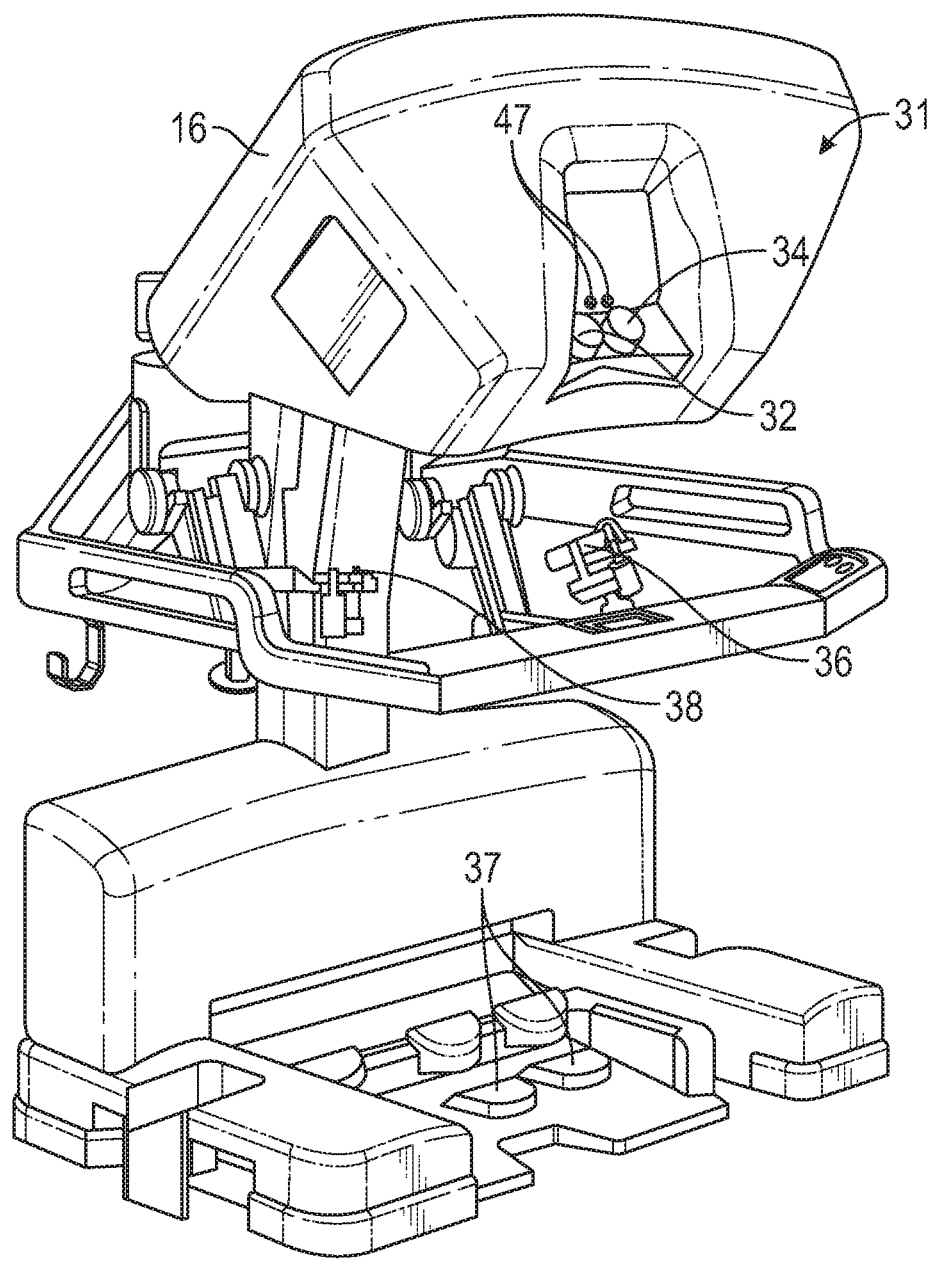
FIG. 2 is a perspective view of a surgeon's console.

FIG. 2 is a perspective view of the user console 16. The surgeon's console 16 includes a viewer display 31 that includes a left eye display 32 and a right eye display 34 for presenting the surgeon 18 with a coordinated stereoscopic view of the surgical site that enables depth perception. The user console 16 further includes one or more hand-operated control input devices 36, 38 to receive larger-scale hand control movements. One or more slave surgical instruments 26 installed for use at on one or more corresponding manipulators manipulator units 22 move in relatively smaller-scale distances that match a surgeon 18's larger-scale manipulation of the one or more master control inputs 36, 38. The master control input devices 36, 38 may provide the same mechanical degrees of freedom as their associated surgical instruments 26 to provide the surgeon 18 with telepresence, or the perception that the master control input devices 36 are integral with the slave surgical instruments 26 so that the surgeon has a keen sense of directly controlling the instruments 26. To this end, position, force, and tactile feedback sensors (not shown) may be employed to transmit position, force, and tactile sensations from the surgical instruments 26 through the control input devices 36,38 to the surgeon's hands, subject to communication delay constraints. Signals (optionally optical or electronic) modulated based upon forces detected at force sensors (not shown) at the instrument 26 may be processed by the processors at the auxiliary unit cart 24 to produce haptic feedback at the control input devices 36 that is indicative of the detected forces.

Figure 3:
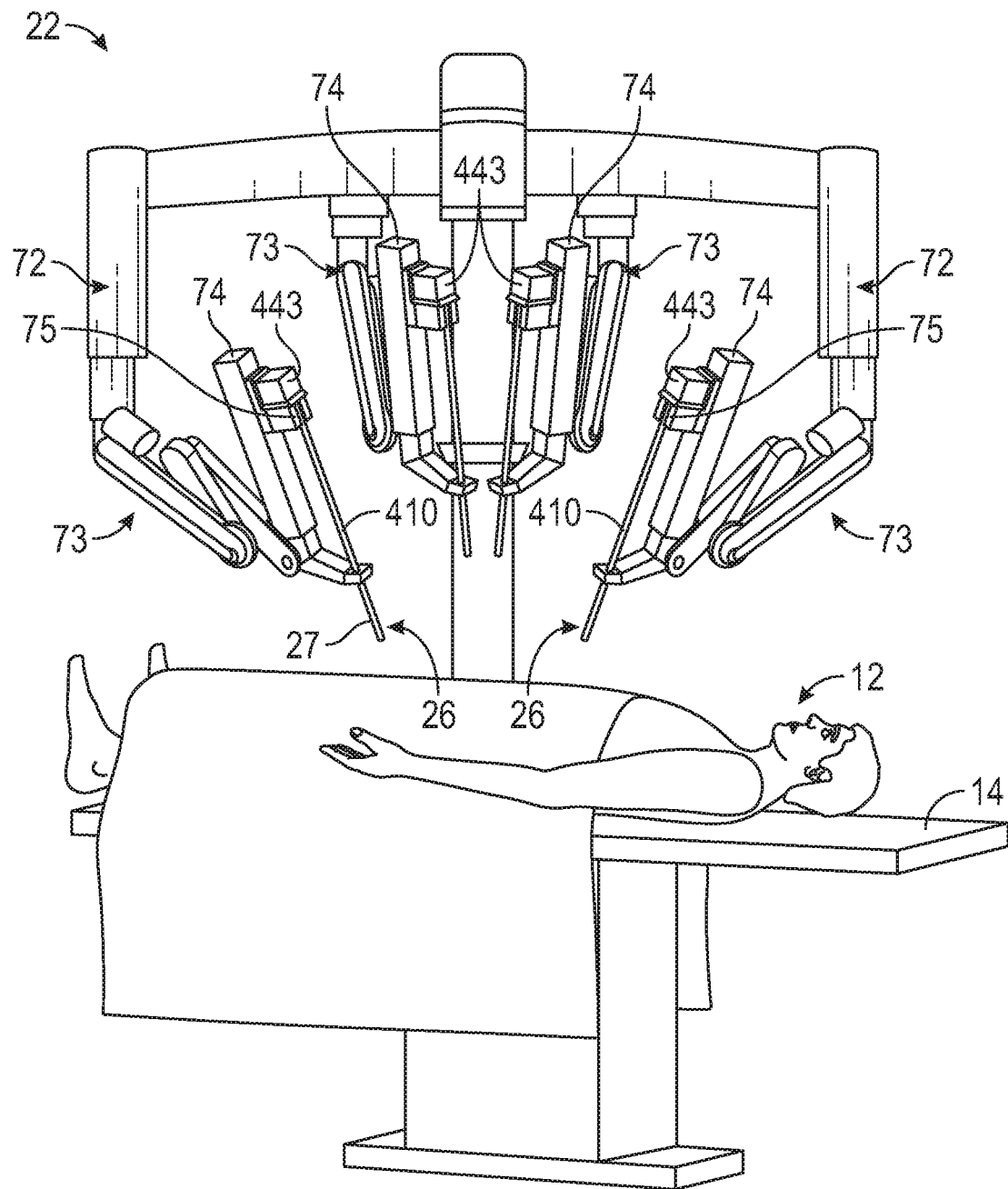
FIG. 3 is a perspective view of a manipulator unit of a minimally invasive teleoperated surgical system.

FIG. 3 is a perspective view of a manipulator unit 22 of the example minimally invasive teleoperated surgical system 10, in accordance with some embodiments. The manipulator unit 22 includes four manipulator support structures 72. Each manipulator support structure 72 includes articulated support structures 73 that are pivotally mounted end-to-end and a pivotally mounted support spar 74. A respective surgical instrument carriage 75, which includes motors to control instrument motion, is mounted at each support spar 74. Additionally, each manipulator support structure 72 can optionally include one or more setup joints (e.g., unpowered and/or lockable) at the junctions of the articulated support structures 73 and at a junction with a spar 74. A carriage 75 can be moved along a spar 74 to position the carriage 75 at different locations along the spar 74. Thus, the spars 74 can be used to position the attached surgical instrument carriage 75 in relation to a patient 12 for surgery. Each surgical instrument 26 is detachably connected to a carriage 75. While the manipulator unit 22 is shown as including four manipulator support structures 72, more or fewer manipulator support structures 72 can be used. In general, at least one of the surgical instruments will include a vision system that typically includes an endoscopic camera instrument for capturing video images and one or more video displays for displaying the captured video images that are coupled to one of the carriages 75.

In one aspect, a carriage 75 houses multiple teleoperated actuators such as motors (not shown) that impart motion to a tension member, such as a cable drive members, that include drive shafts and capstans (not shown), that in turn, drive cable motions that the surgical instrument 26 translates into a variety of movements of an end effector portion of the surgical instrument 26. In some embodiments, the teleoperated actuators in a carriage 75 impart motion to individual components of the surgical instrument 26 such as end effector wrist movement or jaw movement, for example.

A surgeon manipulates the master control input devices 36, 38 to control an instrument end effector. An input provided by a surgeon or other medical person to a control input device 36 or 38 (a "master" command) is translated into a corresponding action by the surgical instrument 26 (a corresponding "slave" response) through actuation of one or more remote motors. A flexible wire cable-based force transmission mechanism or the like is used to transfer the motions of each of the remotely located teleoperated motors to a corresponding instrument-interfacing actuator output located at an instrument carriage 75. In some embodiments, a mechanical adapter interface 76 mechanically couples an instrument 26 to actuators 442 (shown in FIGS. 4-5) within an instrument carriage to control motions inside the instrument 26. The surgical instrument 26 may be mechanically coupled to a first actuator (not shown), which may control a first motion of the surgical instrument such as longitudinal (z-axis) rotation. The surgical instrument 26 may be mechanically coupled to a second actuator (not shown), which may control second motion of the surgical instrument such as planar two-dimensional (x, y) motion. The surgical instrument 26 may be mechanically coupled to a third actuator, which may control third motion of the surgical instrument such as opening and closing of jaws of an end effector, for example.

Figure 4:
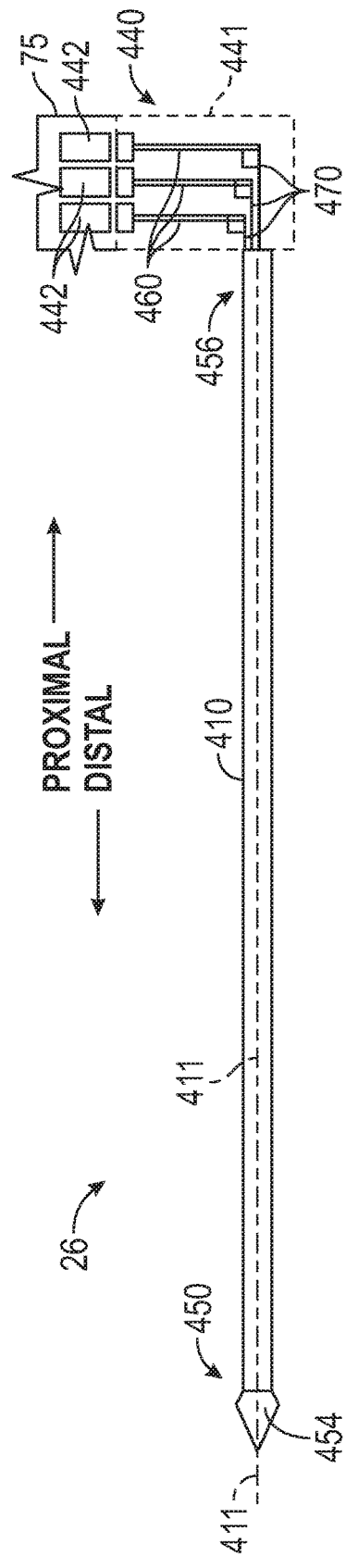
FIG. 4 is a diagrammatic side elevation view of a surgical instrument coupled to an instrument carriage.

FIG. 4 is a diagrammatic side elevation view of a surgical instrument 26 coupled to an instrument carriage 75. As used herein the term "proximal" indicates a direction closer to a manipulator arm, and the term "distal" indicates a direction more distant from the manipulator arm.

The surgical instrument 26 includes an elongated hollow cylindrical tubular shaft 410 having a distal end portion 450 and a proximal end portion 456. Distal end portion 450 includes an end effector 454 for insertion into a patient's body cavity. Proximal end portion 456 is secured to a proximal instrument controller 440. An inner wall of the shaft defines a cylindrical hollow bore. A longitudinal center axis 411 of the shaft (the "shaft center axis") is defined through distal end portion 450 and proximal end portion 450. The proximal instrument controller 440, includes a housing 441 (shown transparent, indicated with dashed lines) that encloses multiple drive members 460, which may include one or more actuators such as, capstans and drive shafts for example, that are configured to couple drive forces imparted by one or more actuators 442 within an instrument carriage 75 to cables 470 extending within the shaft 410 in parallel alignment with the shaft center axis 411. U.S. provisional patent application No. 62/767,895, filed on Nov. 15, 2019, discloses drive members 460 in accordance with some embodiments, which is expressly incorporated herein in its entirety by this reference. The cables 470 extend within the shaft between the drive members and an end effector 454. The cables 470 are operatively coupled so that movement of the cables may impart motion to an end effector 454 such as to open or close of jaws and to cause yaw of the jaws and pitch of the wrist motion, for example. The end effector 454 can include a functional mechanical degree of freedom, such as jaws that open or close, or a knife that translates along a path or a wrist 452 that may move in x and y directions. U.S. Pat. No. 6,394,998 shows examples of end effectors with multiple degrees of mechanical freedom. The distal portion 450 of the surgical instrument 26 can provide any of a variety of different kinds of end effectors 454, such as the forceps, a needle driver, a cautery device, a cutting tool, an imaging device (e.g., an endoscope or ultrasound probe), or the like. Thus, actuators 442 located at the carriage 75 near the proximal end portion 456 of the shaft 410 control movement of the end effector 454 at the distal end portion 450 of the shaft 410 by causing drive members 460 within the housing 441 of the proximal instrument controller 440 to exert control forces upon cables 470 extending within the shaft 410 parallel to the shaft axis 411 between the drive members 460 and the end effector 454.

Instrument Shaft with Sensor Aligned Cable Guide

Figure 5:
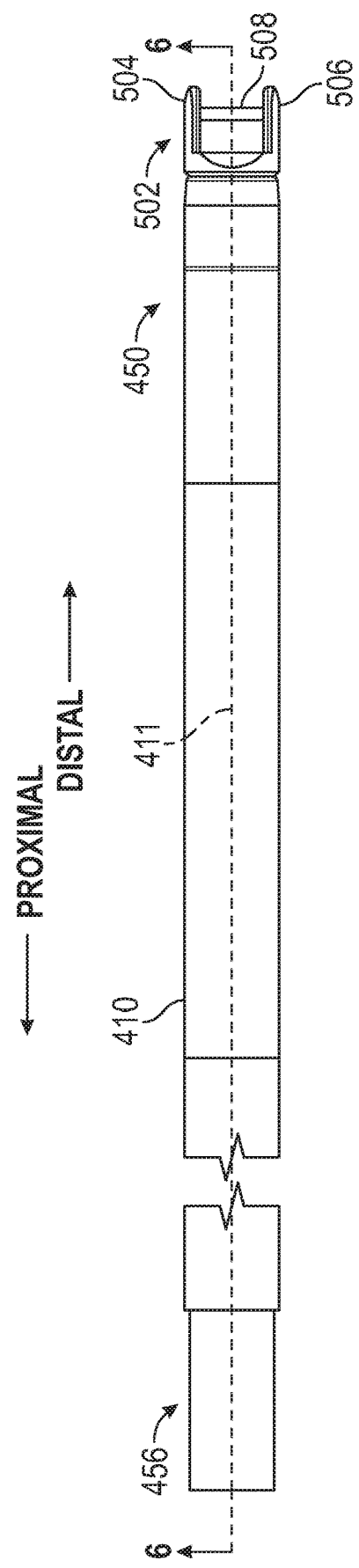
FIG. 5 is an illustrative top view of an elongated hollow shaft.

FIG. 5 is an illustrative top view of the elongated hollow shaft 410. A clevis 502 depends distally from the distal end portion 450 of the shaft 410 for mounting an end effector (not shown) thereon. An end effector often may include an additional clevis (not shown), commonly referred to as a distal clevis, to permit multiple degrees of motion. The clevis 502 includes opposed first and second arms 504, 506 with an axle 508 extending between the arms for mounting an end effector thereon. Clevis 502 illustrates an example one of various components that can be coupled to the distal end of shaft 410, such as wrist components, thereapeutic and diagnostic end effector components, imaging components, and the like.

Figure 6:
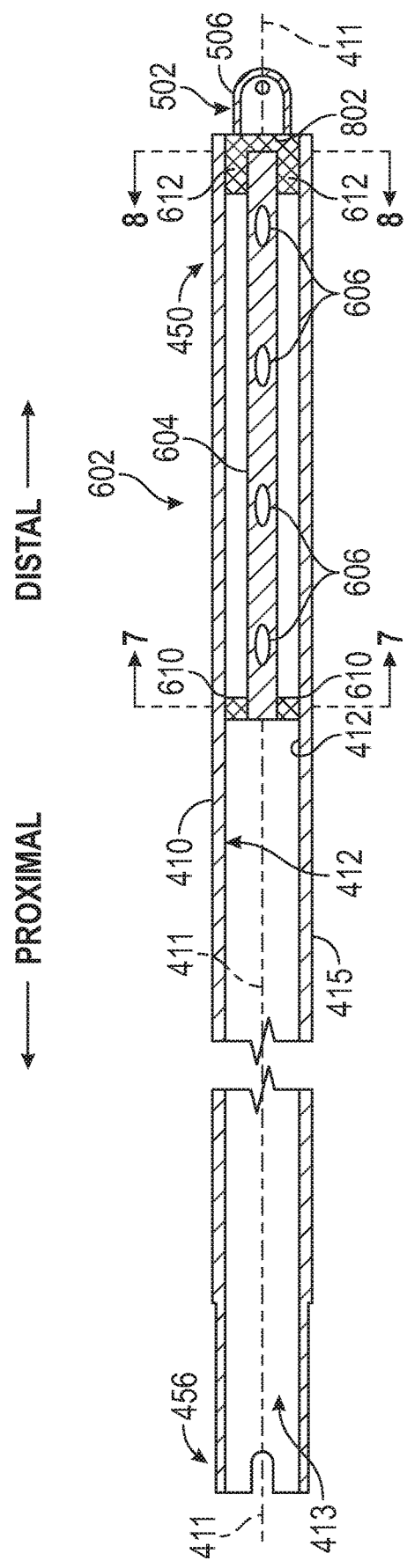
FIG. 6 is an illustrative side cross-sectional view of the elongated hollow shaft along line 6-6 of FIG. 5, showing a force sensor disposed inside.

FIG. 6 is an illustrative side cross-sectional view of the elongated hollow shaft 410 along line 6-6 of FIG. 5, showing a force sensor 602 disposed therein. An inner wall surface 412 of the shaft 410 defines a cylindrical hollow bore 413. Cables (not shown) extending within the shaft 410 are not shown so that the force sensor 602 can be shown more clearly. The force sensor 602 acts as a transducer that includes an elongated beam 604 with multiple strain gauges 606 disposed thereon. The beam 604 is coaxially aligned with the longitudinal shaft center axis 411 and may have various cross-sectional shapes (e.g., round, rectangular, square, and the like). The beam 604 may be formed of a material such as stainless steel, Titanium, or Zirconium alloys, for example. The strain gauges 606 are configured to produce one or more signals having values indicative of magnitude of force imparted to the beam 604 in a direction generally perpendicular to the shaft center axis 411. A proximal anchor 610 in contact with the inner wall surface 412 of the shaft 410, and a proximal end portion of the beam 604 mechanically couples the proximal end portion of the beam 604 to the inner wall 412 portion of the shaft 410. The proximal anchor may be secured to the inner wall surface 412 of the shaft 410 by (interference or close fits, glue, or welds, for example). Similarly, a distal anchor 612 in contact with the inner wall surface 412 of the shaft 410, and a distal end portion of the beam 604 mechanically couples the distal end portion of the beam 604 to the inner wall 412 portion of the shaft 410. The distal anchor 612 may be secured to the inner wall surface 412 of the shaft 410 by (interference or close fits, glue, or welds, for example). The clevis 502 depends from the distal anchor 612.

Figure 7:
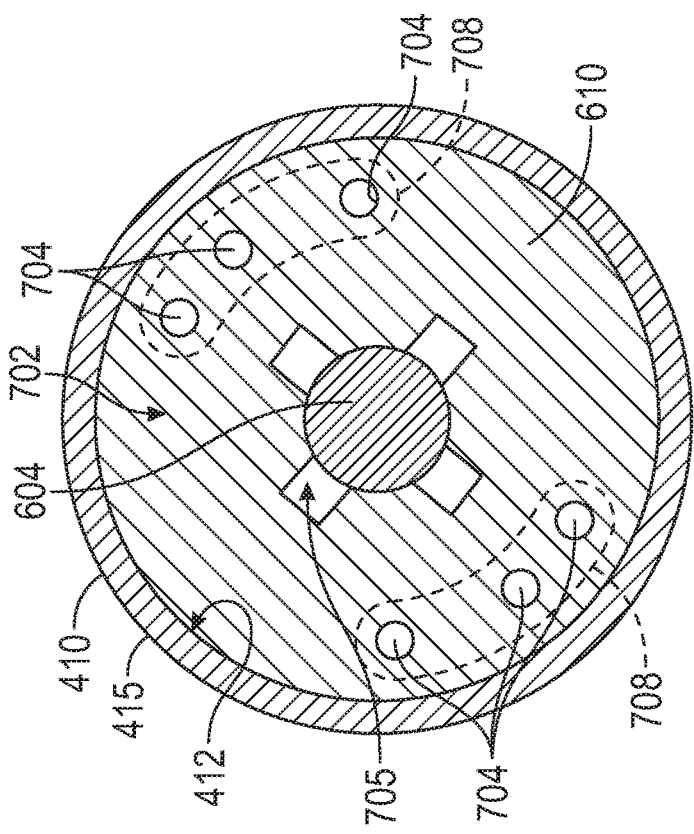
FIG. 7 is an illustrative proximal axial cross-sectional view of the elongated hollow shaft along line 7-7 of FIG. 6, showing a proximal axial view of a proximal anchor.

FIG. 7 is an illustrative proximal axial view of the elongated hollow shaft 410 along line 7-7 of FIG. 6, showing a proximal axial cross-sectional view of the proximal anchor 610. Referring to FIG. 6 and FIG. 7, the proximal anchor 610 includes a proximal annular portion 702 defining an example center opening 705 sized to securely receive a proximal end portion of the beam 604 therein. More particularly, the center opening 705 is defined by lip 706 in proximal transverse annular portion 702. As shown, an example lip 706 has a shape of a superimposed cross and circle, so that center opening 705 has a cross section of a relatively smaller circle superimposed on a relatively larger cross. An outer perimeter of the proximal transverse annular portion 702 is sized and configured to snugly interfit within the shaft 410 such that the proximal annular portion 702 imparts forces received at an outer wall surface 415 of the shaft 410 to a proximal end portion of the beam 604 or vice versa. The proximal annular portion 702 includes a proximal cable guide portion 708, indicated by dashed lines. The example proximal cable guide portion 708 defines a proximal first plurality of cable guide holes 704 in a surface of the proximal annular portion 702. In an example shaft 410, the proximal first plurality of cable guide holes 704 are arranged in a first pattern. The proximal first plurality of cable guide holes 704 are sized for sliding passage of control cables (not shown) therethrough. The first and second cables are configured to control an end effector in three degrees of freedom.

Figure 8:
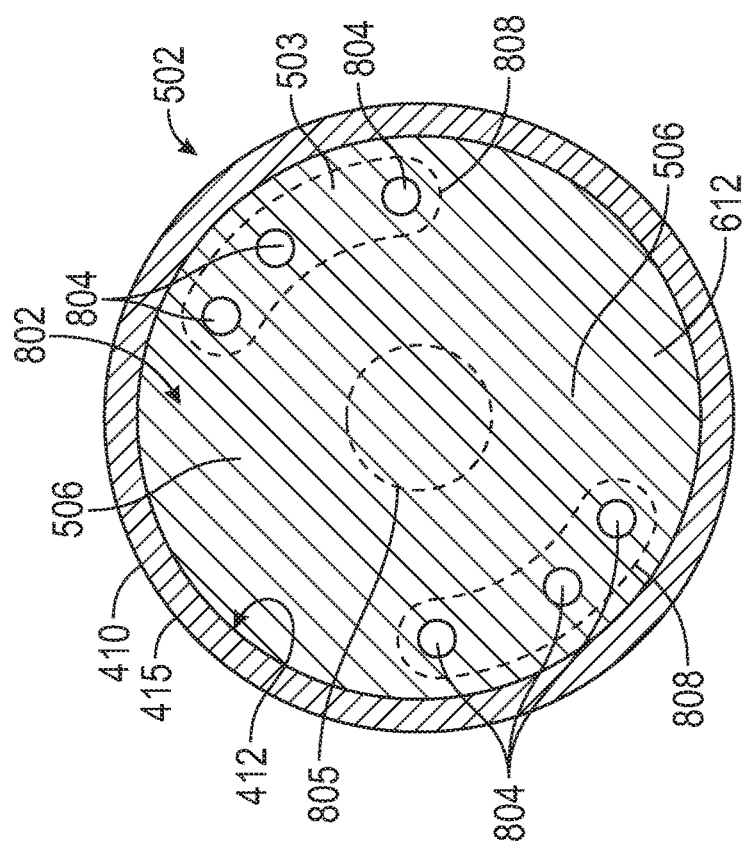
FIG. 8 is an illustrative distal axial view of the elongated hollow shaft along line 8-8 of FIG. 6, showing a distal axial view of a distal anchor.

FIG. 8 is an illustrative distal axial view of the elongated hollow shaft 410 along line 8-8 of FIG. 6, showing a distal axial view of the distal anchor 612. Referring to FIG. 6 and FIG. 8, the distal anchor 612 includes a distal transverse annular portion 802 defining a center portion, indicated by dashed lines 805, an opposite side of which is secured to a distal end portion of the beam (not shown). An outer perimeter of the distal transverse annular surface portion 802 is sized and configured to snugly interfit within the shaft 410. The distal annular portion 802 includes a distal cable guide portion 808, indicated by dashed lines. An example distal cable guide portion 808 defines a distal second plurality of cable guide holes 804 in a surface of the distal annular portion 802. In an example shaft 410, the distal second plurality of cable guide holes 804 are arranged in a second pattern. The distal cable guide holes are sized for sliding passage of the control cables (not shown) therethrough.

Figure 9:
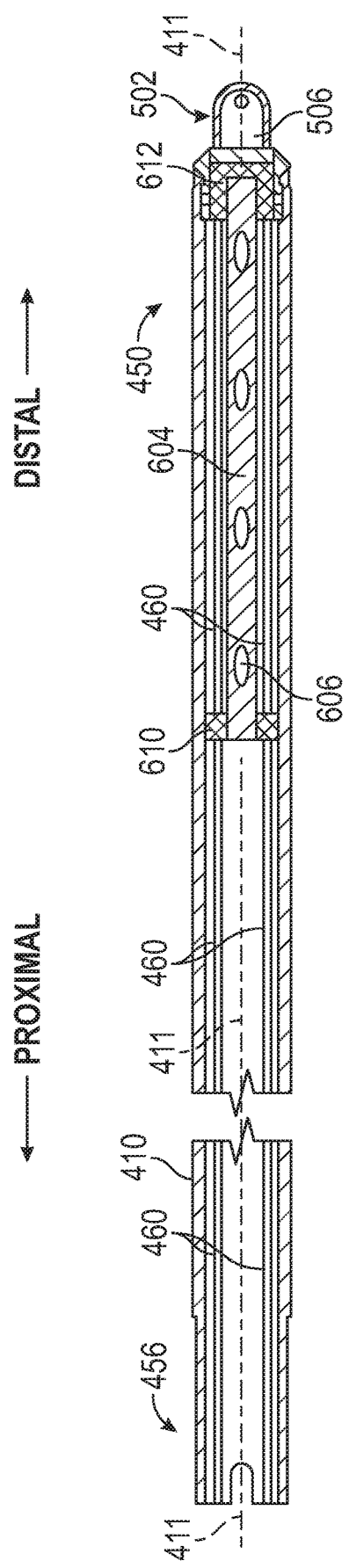
FIG. 9 is an illustrative side cross-sectional view of the elongated hollow shaft of FIG. 5 with the walls of the outer shaft cut away to show cables extending longitudinally parallel with the shaft longitudinal axis.

The proximal cable guide portion 708 and the distal cable guide portion 808 operate together to guide cables parallel to the shaft center axis 411. As illustrated in the drawings, the proximal first plurality of cable guide holes 704 are arranged in a first pattern, the distal second plurality of cable guide holes 804 are arranged in a second cable guide hole pattern, and the first pattern matches the second pattern. The proximal guide portion 708 is aligned with the distal guide portion 808 so that the first pattern including the proximal first plurality of cable guide holes 704 aligns longitudinally with the second pattern that includes the distal second plurality of cable guide holes 804. Each proximal cable guide hole 704 is aligned with a corresponding distal cable guide hole 804 such that cable guide surface axes 1150 (see FIG. 11C) through the centers of the corresponding aligned proximal and distal holes 704, 804 are aligned parallel to the shaft center axis 411. Together, the proximal cable guide portion 708 and the distal cable guide portion 808 cooperate to maintain cables in alignment parallel to a portion of the shaft center axis 411 where the sensor beam 604 extends. FIG. 9 is an illustrative side cross-sectional view of the elongated hollow shaft 410 of FIG. 5 with the wall of the outer shaft cut away to show cables 460 extending longitudinally parallel with the shaft axis 411. The cables 460 may branch in different directions at the proximal end portion of the shaft for routing to be actuated by different actuators, for example. And, the cables may branch in different directions at the distal end portion of the shaft for routing to different components of the end effector, for example. The above-mentioned U.S. Pat. No. 6,394,998 shows examples of cables branching in complex tortuous paths at an end effector. Each proximal cable guide hole 704 of a proximal cable guide portion 708 of the proximal anchor 610 is longitudinally aligned with a corresponding distal cable guide hole 804 of a distal cable guide portion 808 of the distal anchor 612 to guide a cable 470 extending between a pair of aligned guide holes to extend in parallel with the longitudinal center axis 411 of the shaft 410, which also is a longitudinal axis of the sensor beam 604. In some example shafts, the cables 460 are formed of a flexible rope construction made of stainless steel, Tungsten, Vectran, or UHMWPE. In some example shafts, in a portion of the shaft where no bending of the cable is required, an elongated solid tubule formed of stainless steel alloy or similar material may be inserted and is coupled on either end with flexible cable segments that extend through the proximal and distal end portions of the shaft along associated routing paths, for example.

Figure 10A:
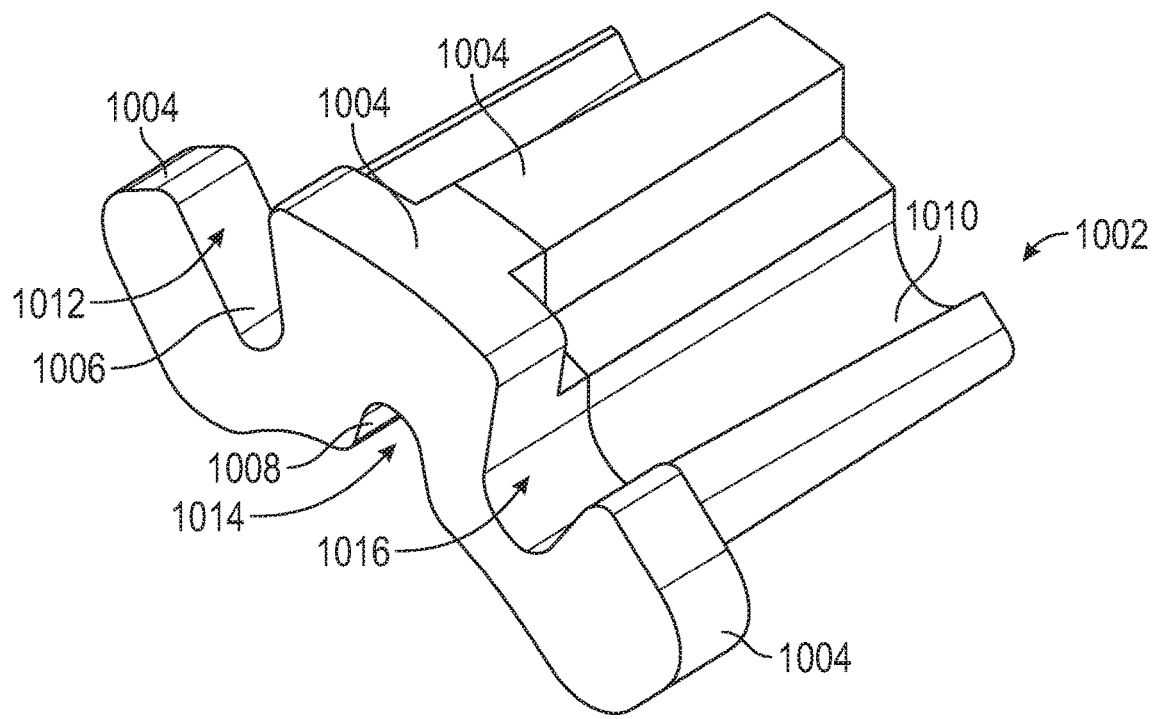
FIG. 10A is a perspective view of a guide slot insert.
Figure 10B:
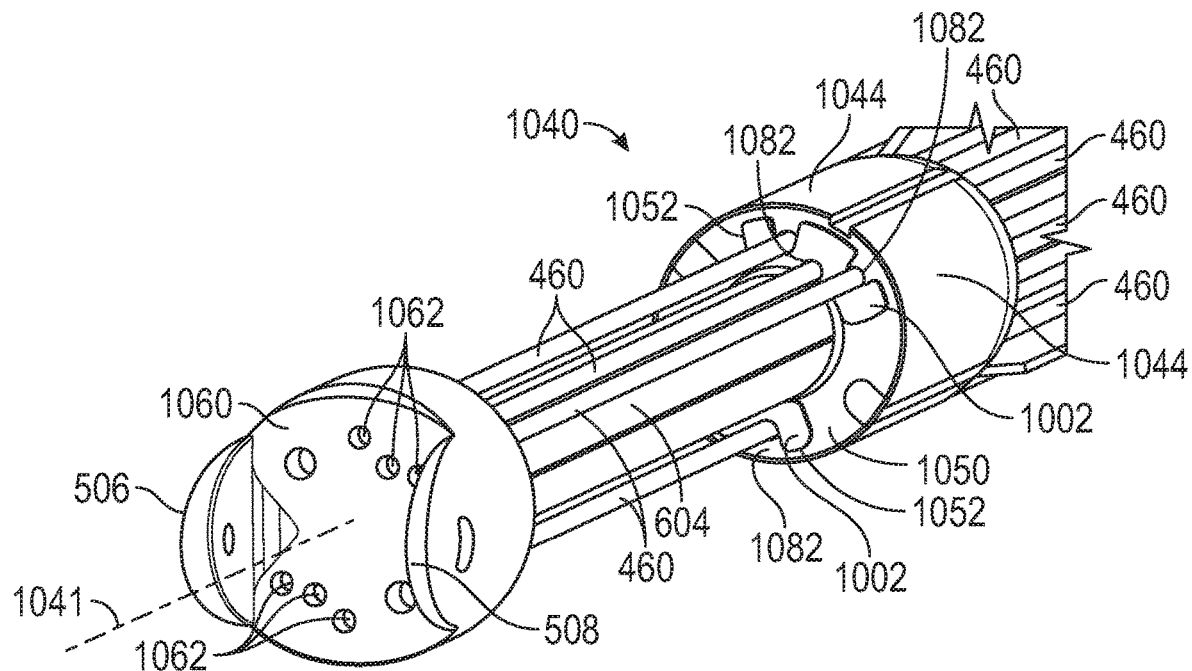
FIG. 10B is a perspective view of a distal end portion of an embodiment of a shaft with portions of the shaft walls removed to show cables and a sensor beam disposed therein.

FIG. 10A is a perspective view of guide slot insert 1002. FIG. 10B is a perspective view of a distal end portion of an embodiment of a shaft 1040 with portions of the shaft wall removed to show cables 460 and a sensor beam 604 disposed therein. Referring to FIG. 10A, the guide slot insert 1002 includes outer engagement surfaces 1004 and includes first, second, and third proximal guide slot surfaces 1006, 1008, 1010 that define corresponding first, second and third guide slots 1012, 1014, 1016 each sized to allow sliding passage of an individual one of cables 460 therethrough. Referring to FIG. 10B, a proximal anchor 1050 defines first and second cut-out regions 1052 each having complementary engagement surfaces (not shown) contoured to interfit with the outer engagement surfaces 1004 of first and second instances of the guide slot insert 1002. As shown, guide slot inserts 1002 are each inserted in a corresponding cut-out region 1052, such that each guide slot insert 1002 guide slot 1012, 1014, 1016 at a proximal anchor 1050 is longitudinally aligned with a corresponding distal guide hole 1062 at a distal anchor 1060. In this way a cable 460 extending between a proximal guide slot and a corresponding distal guide hole extends parallel to a longitudinal center axis 1041 of the shaft 1040. Each of the proximal cable guide slots 1012, 1014, 1016 of defined by the proximal anchor 1050 is longitudinally aligned with a corresponding distal cable guide hole 1062 of a distal cable guide portion 808 of the distal anchor 1060 to guide a cable 460 extending between an aligned proximal guide cable slot distal guide hole pair to extend in parallel with the longitudinal center axis 1041 of the shaft 1040, which also is a longitudinal axis of the sensor beam 604. A portion of each respective cable 460 extends in parallel with the center axis 1041 between a respective proximal slot surface and a corresponding respective distal guide hole. More particularly, as shown in FIG. 10B, in some optional embodiments the guide slot surfaces and the surface of cut-out region 1052 cooperate to define individual proximal guide holes 1082 for corresponding individual cables 460. These proximal guide holes 1082 are longitudinally aligned with corresponding distal guide holes 1062. In other optional embodiments shaft wall portions 1044 of the shaft 1040 may overlay the outer proximal guide slot surfaces 1006, 1010 so that guide slot surfaces and the portions of the shaft wall inner surface cooperate to define proximal guide holes 1082 aligned with corresponding distal guide holes 1062. An advantage of such embodiments is the elimination of the need to form closed voids in the proximal anchor 1050 and so reduce manufacturing complexity and cost. And it should be appreciated that in some optional embodiments, one or more guide slot inserts similar to guide slot inserts 1002 may be used in the distal anchor component instead of forming multiple discrete cable guide holes in the distal anchor component.

Use Examples

By ensuring that the control cables remain parallel to the force sensor beam at all shaft roll orientations around the shaft center axis, forces on the cables that actuate the distal end components of the instrument do not affect the transverse forces on the force sensor beam when the instrument is in use. In this way the transverse forces on the sensor beam, which are sensed by the force sensing elements on the sensor beam, are effectively limited to the clinical forces associated with the distal end components of the instruments interacting with tissue and objects at the surgical site. As a result, the force sensors on the force sensor beam can accurately sense these clinical forces and in turn relay the sensed clinical forces to a computer processor, which in turn outputs the sensed forces via a user input device to the surgeon's hand operating the user input device as an accurate haptic representation of the clinical forces at the distal end of the instrument.

Figure 11A:
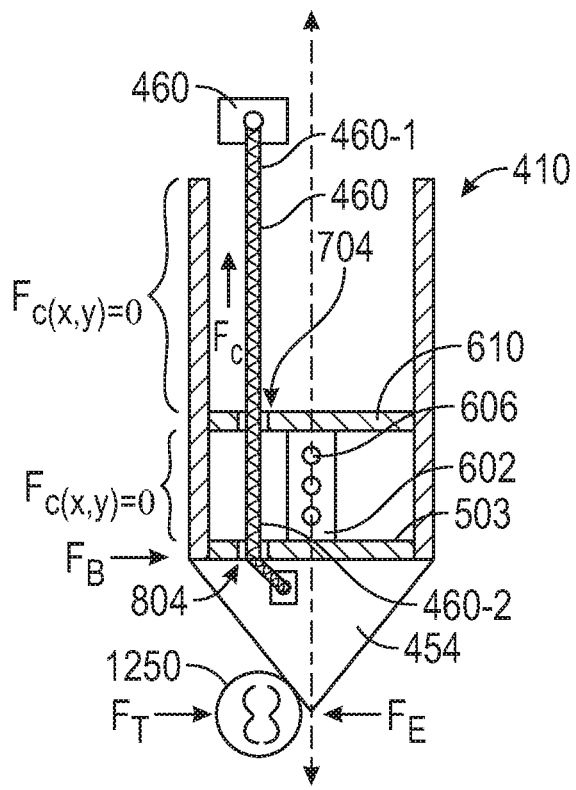
FIG. 11A is an illustrative simplified longitudinal cross section side view schematic drawing of a surgical instrument shaft in a neutral resting position.
Figure 11B:
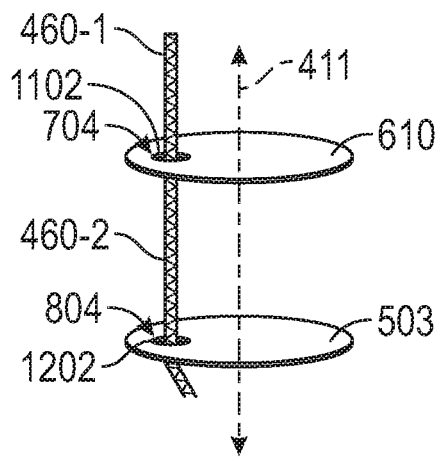
FIG. 11B is an illustrative simplified perspective schematic drawing of the surgical instrument shaft of FIG. 11A showing an example cable passing through proximal and distal guide holes of proximal and distal anchors.
Figure 11C:
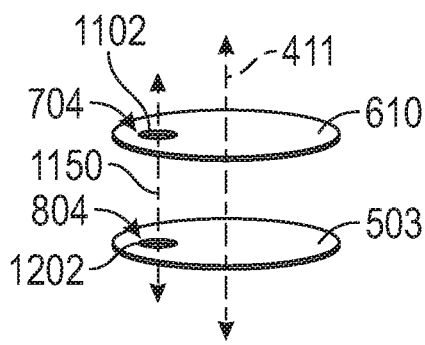
FIG. 11C is an illustrative simplified perspective view schematic drawing of the surgical instrument shaft showing a cable guide surface axis.

FIG. 11A is an illustrative simplified cross-sectional side view schematic drawing of a surgical instrument shaft 410 in a neutral resting position in which an example control cable 460 extends within the shaft parallel to a center axis 411 of the shaft. A neutral resting position is one in which control cables 460 are not twisted within shaft 410, such as mid-way between two rotational range of motion limits of shaft 410. FIG. 11B is an illustrative simplified perspective view schematic drawing of the surgical instrument shaft 410 in the neutral resting position of FIG. 11A, showing the example cable 460 passing through proximal guide hole 704 in a proximal guide portion 704 of the proximal anchor 610 and through distal guide hole 804 in a distal cable guide portion 804 of a distal transverse surface portion 503 within the hollow shaft 410. FIG. 11C is an illustrative simplified perspective view schematic drawing of the surgical instrument shaft 410, while in the neutral position, showing a cable guide surface axis 1150 extending parallel to the shaft center axis 411, between a center of a proximal guide hole 704 defined in proximal guide surface 1102 and a center of a distal guide hole 804 defined in a distal guide surface 1202. Thus, hole 704 and hole 804 are a pair of longitudinally aligned holes, and proximal guide surface 1102 and distal guide surface 1202 are a pair of longitudinally aligned guide surfaces. In the example of FIG. 8, the distal transverse annular portion 802 provides the distal transverse surface portion 503, for example. However, in an alternative example (not shown), a distal end portion of the sensor beam 604 is tapered and extends within a complementary tapered opening in the clevis, which is secured to the distal end portion of the shaft 410. Thus, a clevis 502 secures the beam 604 within the shaft. 410. Thus, in the alternative example, a clevis 502 provides the distal transverse surface portion 503, for example.

Figure 12A:
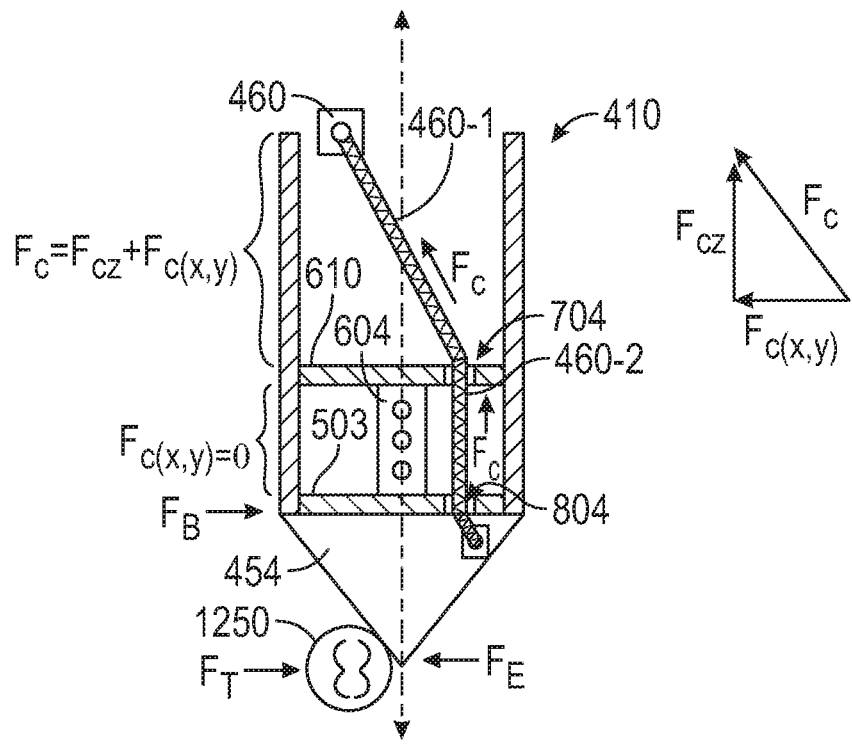
FIG. 12A is an illustrative simplified longitudinal cross section side view of a surgical instrument shaft partially about the shaft center axis, in which an example control cable extending within the shaft is rotated in an approximate partial spiral about the shaft center axis.
Figure 12B:
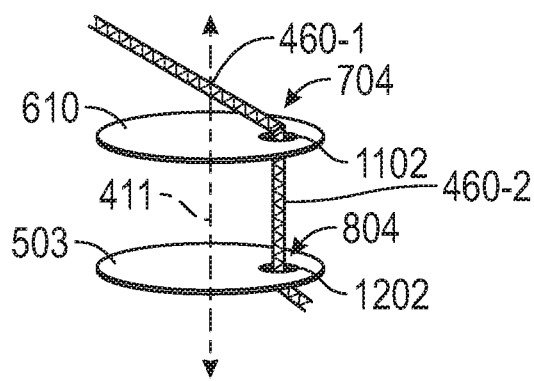
FIG. 12B is an illustrative simplified perspective view schematic drawing showing the example control cable passing through proximal and distal guide holes formed in proximal and distal anchors within the surgical instrument shaft.
Figure 12C:
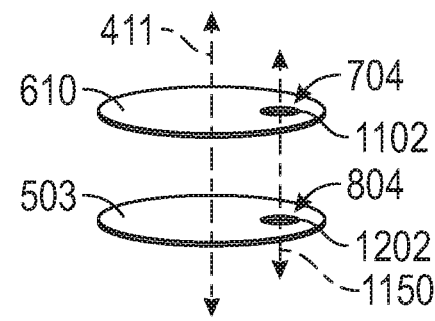
FIG. 12C is an illustrative simplified perspective view schematic drawing of the surgical instrument shaft, partially rotated, showing a cable guide surface axis extending parallel to the shaft center axis.

FIG. 12A is the illustrative simplified longitudinal cross-sectional sideview of the surgical instrument shaft 410 partially rotated (approximately one-half turn) about the shaft center axis 411, in which the example control cable 460 extending within the shaft is rotated in an approximate partial spiral about the center axis 411 of the shaft 410. FIG. 12B is an illustrative simplified perspective view schematic drawing showing the example cable 460 passing through proximal and distal guide holes 704, 804 formed in the proximal anchor 610 and the distal transverse surface 503 within the hollow shaft 410 as described for FIG. 11B. FIG. 12C is an illustrative simplified perspective view schematic drawing of the surgical instrument shaft 410, while partially rotated, showing the cable guide surface axis 1150 extending parallel to the shaft center axis 411.

Since the alignment of the cables 460 is fixed as they exit the proximal instrument controller 440 portion of the instrument, the cables will twist inside shaft 410 as shaft 410 rotates around the central shaft axis 411 relative to the proximal instrument controller 440. But as shown, the guide holes in the proximal and distal anchors that longitudinally bracket the force sensor beam remain longitudinally aligned and will keep the cables from twisting in the force sensor beam portion of the instrument shaft.

To simplify the explanation and the drawings, only a single example control cable 460 is shown, in FIGS. 11A-11B and in FIGS. 12A-12B, although it will be appreciated that in actual embodiments, multiple cables extend within the hollow shaft 410. Moreover, to better illustrate external forces exerted upon the example cable 460, the rotation of the shaft and the corresponding spiral rotation of the cable shown in FIGS. 12A-12B are exaggerated somewhat beyond what ordinarily might occur in practice.

A proximal end portion of the example cable 460 is secured to an example drive member 462 within the proximal instrument controller 440 disposed at a proximal end portion of the shaft 456. A distal end portion of the cable 460 is secured to an end effector 454 at a distal end portion of the shaft 450. It is noted that the example cable 460 may follow a tortuous path such as a path shown in FIGS. 11A-11B of U.S. Pat. No. 6,394,998 within the end effector 454, for example, that may include interfacing with one or more pulleys or other mechanical control structures to contribute to three-degree-of-freedom movement of the end effector, for example.

A force sensor 602 is disposed within the shaft 410 aligned with the shaft center axis 411. In some embodiments, the sensor 602 includes a beam 604 with strain gauges 606 thereon. The beam 604 has proximal and distal end portions secured to respective proximal anchor 610 and distal transverse surface 503. The proximal anchor 610 is secured to an inner wall of the shaft 410 at a first axial location of the shaft. In some embodiments, the proximal anchor 610 includes a first planar surface 702 aligned perpendicular to the shaft center axis 411 and that includes a proximal guide surface 1102 that defines a proximal guide hole 704. Similarly, in some embodiments, the distal transverse surface 503 includes a second planar surface aligned perpendicular to the shaft center axis 411 and that includes a distal guide surface 1202 that defines a distal guide hole 804. The example cable 460 passes through the proximal and distal guide holes 704, 804. The proximal and distal guide surfaces 1102, 1202 define the proximal and distal guide holes 704, 804 sized to permit the cable 460 to slide therethrough.

The proximal and distal guide surfaces 1102, 1202 are longitudinally aligned to guide a portion of the cable 460 extending between them alongside the beam 604, to align parallel to the shaft center axis 411 and parallel to the beam regardless of whether the shaft 410 is in the rest position of FIG. 11B or the rotated position of FIG. 12B. More particularly, the proximal and distal guide surfaces 702, 802 define proximal and distal holes 704, 804 that are wide enough to permit sliding passage of the example cable 460 and that are narrow enough that the guide surfaces 1102, 1202 about the holes 704, 804 urge the cable 460 to align parallel to the shaft center axis 411 both when the shaft is disposed in the neutral position and when the shaft is disposed in the rotated position. In some embodiments, the proximal and distal guide surfaces 1102, 1202 cooperate with walls of the shaft 410 or clevis 502 to provide the guide holes 704, 804.

During a medical procedure, a surgeon may manipulate the master control input devices 36, 38 to provide input commands to control movement of a slave end effector 454 at the distal end 450 of the shaft 410. Movement of the end effector 454 may cause it to physically contact patient tissue 1250 for a clinical purpose such as to cut, suture, probe, or cauterize the contacted tissue, for example. It will be appreciated that different kinds of end effectors may be provided for these different purposes, for example. During contact of the end effector 454 with patient tissue 1250, the end effector may impart an end effector force $F_E$ to the tissue 1250, and in reaction, the tissue may impart a corresponding tissue force $F_T$ upon the end effector 454. The end effector force $F_E$ and the corresponding tissue force $F_T$ each includes a force component perpendicular to the shaft center axis 411 and each may include a force component parallel to the shaft center axis 411. An example reference coordinate system is provided in FIGS. 11A-11B and FIGS. 12A-12B. A z-axis is shown aligned parallel with the longitudinal axis. An (x, y) plane is shown aligned perpendicular to the longitudinal axis.

Specifically, for example, the tissue force $F_T$ includes a planar component $F_{T(x,y)}$ perpendicular to the shaft center axis 411 and a z-direction component $F_{Tz}$ parallel to the shaft center axis 411.

$$F_T = \sqrt{F_{T(x,y)}^2 + F_{Tz}^2} \quad (1)$$

A perpendicular tissue force component $FT_{(x,y)}$ at imparted at the end effector 454 may cause corresponding perpendicular bending forces $FB_{(x,y)}$ at a portion of the shaft 410 in which the sensor 602 is disposed. The perpendicular bending forces may cause deflection or cause bending of a portion of the shaft 410 alongside the sensor 602. The proximal anchor 610 and the distal guide transverse 503 mechanically couple the perpendicular bending forces to the sensor 602 causing strain gauges 606 mounted on a sensor beam 604 to produce one or more signals indictive of magnitude of the bending forces. The strain gauges may be configured to convert the coupled perpendicular mechanical bending forces FB(x,y) into electrical or optical signals having signal values indicative of magnitude of the coupled-in perpendicular bending forces. It is noted that magnitude of a parallel tissue force component FTz may be determined by one or more separate sensors disposed at the proximal end portion 450 of the shaft 410, at the instrument controller 440, as described in U.S. provisional patent application No. 62/767,891, filed on Nov. 15, 2019.

It will be appreciated that the proximally located instrument controller 440 ordinarily remains in a fixed position relative to patient tissue 1250 during a medical procedure, although the shaft 410 may rotate about the shaft center axis 411 due to the roll degree of freedom (DOF) of the wrist, for example. The end effector 454 is fixedly secured at the clevis 502 which is fixedly secured to the distal anchor such that the end effector 454 rotates in unison with the shaft 410 via rotation of the proximal anchor and beam. Thus, the end effector 454 and the shaft rotate together about the shaft center axis 411 while the instrument controller 440 does not rotate.

More specifically, rotation of the shaft 410 about the shaft center axis 411 causes a corresponding spiral-like rotation of a proximal first portion 460-1 of the example cable disposed between the proximal anchor 610 and the proximal end portion of the shaft 456. Importantly, however, as also shown by a comparison of the drawings of FIGS. 11A-11B with the drawings of FIGS. 12A-12B, the proximal and distal guide surfaces 1102, 1202 cooperate to guide a distal second portion 460-2 of the example cable 460 that extends between them and alongside the sensor beam 604 into alignment in parallel with the shaft center axis 411 despite the ion of the shaft 410 and despite the corresponding twisting of the example 460 cable.

The example proximally located drive member 460 in FIGS. 11A-11B and FIGS. 12A-12B may impart cable forces $F_C$ to the example cable 460 to effect movement of the distally mounted end effector 454. The cable forces may comprise a sum of static tensioning cable forces $F_{CS}$ and dynamic clinical cable forces $F_{CD}$.

$$F_C = F_{CS} + F_{CD} \quad (2)$$

In some embodiments the example cable 460 typically may be pre-tensioned with the static cable force $F_{CS}$. During a surgical procedure, an additional dynamic clinical force $F_{CD}$ may be imparted to the cable, in response to a surgeon command at a master control input devices 36, 38, to effect movement of the cable and corresponding movement of the end effector 454. Typically, the magnitude of the static pre-tension cable force $F_{CS}$ is significantly less than the magnitude of the dynamic clinical cable forces $F_{CD}$. For example, in some embodiments, the static cable force $F_{CS}$ ordinarily has a magnitude in a range of about 2-5 lbf, and the dynamic cable force $F_{CD}$ ordinarily has a magnitude in a range of about 20-30 lbf. Moreover, the magnitude of the cable threes typically also is significantly larger than both the magnitude of the perpendicular tissue force $F_{T(x,y)}$ and a corresponding bending three $F_B$. For example, in some embodiments, a perpendicular tissue force $F_{T(x,y)}$ and a corresponding bending force ordinarily have a magnitudes in a range of about 0-5 lbf.

In the neutral resting position shown in FIGS. 11A-11B, the entire cable force $F_C$ is imparted along the z-direction, parallel to the shaft center axis, and as a result, the cable force has no perpendicular, (x, y) planar, component to impart to the sensor 602. Thus, in the neutral resting position, the cable force does not impact measurement of the perpendicular bending force $F_B$ by the sensor 602, since the cable force is directed entirely in the z-direction, parallel to the shaft center axis 411.

In the rotated position shown in FIGS. 12A-12B, an axial first component of the cable force $F_{Cz}$ is imparted to the first, proximal portion 460-1 of the example cable 460, in a direction parallel to the shaft center axis 411, in the in z-direction. Moreover, in the rotated position, a planar second component of the cable force $F_{C(x,y)}$ is imparted to the proximal anchor 610 in direction perpendicular to the shaft center axis 411, within the perpendicular (x, y) plane.

$$F_C = F_{Cz} + F_{C(x,y)} \quad (3)$$

In the absence of the guide 1102 matching 1202, the planar second component of the cable force $F_{C(x,y)}$ is imparted to the distal anchor 612, which couples into the clinical perpendicular bending force $F_B$. Thus, in the example rotated position, the planar second component of the cable force $F_{C(x,y)}$ has the potential to impart cable-related forces to the sensor 602, which have the potential to introduce errors to measurements of the perpendicular bending three $F_B$ caused by the perpendicular tissue force component $F_{T(x,y)}$.

Advantageously, however, the first and second guide surfaces 1102, 1202 isolate the sensor 602 from the error-causing planar perpendicular component of the cable forces $F_{C(x,y)}$ by urging the second distal portion 460-2 of the example cable 460, which runs alongside the sensor beam 602, into parallel alignment with the shaft center axis 411. Urging the second, distal portion 460-2 of the cable 460 into parallel alignment with the shaft center axis 411 ensures that all cable forces at the second, distal portion 460-2 of the cable 460 are z-direction forces aligned parallel to the shaft center axis 411. In other words, the cable forces at the second, distal portion 460-2 of the cable 460 have no (x, y) planar component that is perpendicular to the shaft center axis 411. Therefore, the cable forces imparted at the second, distal portion 460-2 of the cable 460, do not interfere with measurement of the perpendicular tissue force FB by the sensor 602.

Example embodiments have been described in illustrations in which a force sensing feature is incorporated at the distal end of a surgical instrument shaft. In other optional embodiments, a component other than a force sensing feature may be used if design requirements specify the instrument control cables should be parallel to the component between the proximal control unit of the instrument and the instrument's distal end effector. Similarly, in yet other optional embodiments the aspects described herein are applied to a middle or proximal end portion of the instrument shaft so that control cables that operate a distal end feature of the instrument are kept parallel to a component disposed in the middle or proximal end portion of the shaft.

The above description is presented to enable any person skilled in the art to create and use a surgical instrument with a cable guide to align control cables extending within an instrument shaft in parallel with a sensor beam disposed within the shaft, to prevent perpendicular cable forces from being imparted to the sensor. Various modifications to the embodiments will be readily apparent to those skilled in the art, and the generic principles defined herein may be applied to other embodiments and applications without departing from the scope of the invention. In the preceding description, numerous details are set forth for the purpose of explanation. However, one of ordinary skill in the art will realize that the embodiments in the disclosure might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the scope of the invention, which is defined in the appended claims.

What is claimed is:

1. A surgical instrument comprising:
   a force sensor comprising a beam and one or more strain gauges on the beam,
      the beam comprising a proximal end, a distal end, and an exterior surface, and
      a center axis of the beam being defined by the proximal end and the distal end of the beam;
   a proximal anchor coupled to the proximal end of the beam;
   a distal anchor coupled to the distal end of the beam;
   an end effector component distal of the distal anchor and coupled to the distal end of the beam; and
   a cable coupled to impart movement of the end effector component,
   wherein the cable extends through the proximal anchor and the distal anchor and is thereby constrained to extend radially outwardly from the one or more strain gauges and parallel to the center axis of the beam.

2. The surgical instrument of claim 1, wherein:
   the proximal anchor comprises a guide surface;
   the distal anchor comprises a guide surface; and
   the guide surface of the proximal anchor and the guide surface of the distal anchor constrain the cable to extend outside the exterior surface of the beam and parallel to the center axis of the beam.

3. The surgical instrument of claim 2, wherein:
   the guide surface of the proximal anchor defines a hole;
   the guide surface of the distal anchor defines a hole; and
   the cable extends through the hole of the proximal anchor and the hole of the distal anchor.

4. The surgical instrument of claim 1, wherein:
   the surgical instrument further comprises a shaft; and
   the proximal end of the beam is coupled to the shaft.

5. The surgical instrument of claim 1, wherein:
   the surgical instrument further comprises a shaft and a drive member;
   the shaft comprises a proximal end portion and a distal end portion;
   the drive member is located proximal of the proximal end of the shaft;
   the proximal end of the beam is coupled to the distal end portion of the shaft; and
   the cable extends from the drive member to the end effector component.

6. The surgical instrument of claim 1, wherein:
   the surgical instrument further comprises a guide slot insert;
   the guide slot insert comprises a guide slot;
   the proximal anchor comprises an opening; and
   the cable extends through the guide slot and the opening of the proximal anchor.

7. The surgical instrument of claim 1, wherein:
   the surgical instrument further comprises a shaft and a guide slot insert inserted into the shaft;
   the shaft comprises an inner surface;
   the guide slot insert comprises a guide slot;
   the proximal anchor comprises an opening defined by the guide slot and the inner surface of the shaft; and
   the cable extends through the opening of the proximal anchor.

8. The surgical instrument of claim 1, wherein:
   the proximal anchor comprises an opening;
   the distal anchor comprises an opening;
   the proximal end of the beam is inserted into the opening of the proximal anchor; and
   the distal end of the beam is inserted into the opening of the distal anchor.

9. The surgical instrument of claim 1, wherein:
   the proximal anchor comprises a planar guide surface;
   the planar guide surface is perpendicular to the center axis of the beam and comprises a guide surface; and
   the cable is constrained by the guide surface.

10. The surgical instrument of claim 1, wherein:
    the cable is pre-tensioned.

11. The surgical instrument of claim 4, wherein:
    the proximal anchor is arranged to rotate in unison with the shaft; and
    the distal anchor is arranged to rotate in unison with the shaft.

12. The surgical instrument of claim 1, wherein:
    the one or more strain gauges are on the exterior surface of the beam.

13. The surgical instrument of claim 1, wherein:
    the cable is a first cable;
    the surgical instrument further comprises a second cable;
    the proximal anchor comprises a guide surface;
    the distal anchor comprises a guide surface;
    the guide surface of the proximal anchor defines a first hole of the proximal anchor, the proximal anchor comprises a second hole, and the first and second holes of the proximal anchor are arranged in a pattern;
    the guide surface of the distal anchor defines a first hole of the distal anchor, the distal anchor comprises a second hole, and the first and second holes of the distal anchor are arranged in the pattern;

the first cable extends through the first hole of the proximal anchor and the first hole of the distal anchor and is thereby constrained to extend outside the exterior surface of the beam and parallel to the center axis of the beam; and the second cable extends through the second hole of the proximal anchor and the second hole of the distal anchor and is thereby constrained to extend outside the exterior surface of the beam and parallel to the center axis of the beam.

14. The surgical instrument of claim 13, wherein:
the first cable and the second cable are each pre-tensioned.

15. The surgical instrument of claim 13, further comprising:
a shaft comprising a proximal end portion, and a distal end portion;
a first drive member disposed at the proximal end portion of the shaft and coupled to a proximal end portion of the first cable;
a second drive member disposed at the proximal end portion of the shaft and coupled to a proximal end portion of the second cable; and
an end effector disposed at the distal end portion of the shaft and coupled to a distal end portion of the first cable and a distal end portion of the second cable.

16. The surgical instrument of claim 13, wherein:
the surgical instrument further comprises a proximal guide slot insert coupled to the proximal anchor;
the proximal guide slot insert comprises a first guide slot and a second guide slot;
the first guide slot is aligned with the first hole of the proximal anchor, and the second guide slot is aligned with the second hole of the proximal anchor; and
the first cable extends through the first guide slot, and the second cable extends through the second guide slot.

17. The surgical instrument of claim 1, wherein:
the cable is constrained to extend outside the exterior surface of the beam between the proximal anchor and the distal anchor.

18. A surgical system comprising:
the surgical instrument of claim 1;
a manipulator unit to manipulate the surgical instrument operably coupled to the manipulator unit; and
a user console comprising one or more input devices to control movement of an end effector of the surgical instrument, wherein one or more forces measured by the force sensor are provided as feedback to a user via at least one of the one or more input devices of the user console.

19. A surgical instrument comprising:
a force sensor comprising a beam and one or more strain gauges on the beam, the beam comprising a proximal end and a distal end, and a center axis of the beam being defined between the proximal end and the distal end of the beam;
a proximal anchor coupled to the proximal end of the beam, the proximal anchor comprising a first plurality of guide holes;
a distal anchor coupled to the distal end of the beam, the distal anchor comprising a second plurality of guide holes aligned with the first plurality of guide holes; and
a plurality of cables,
each cable of the plurality of cables extending through a corresponding unique guide hole of the first plurality of guide holes and through a corresponding unique guide hole of the second plurality of guide holes, and
each cable of the plurality of cables constrained to remain parallel to the center axis of the beam by the corresponding unique guide hole of the first plurality of guide holes and the corresponding unique guide hole of the second plurality of guide holes.

20. The surgical instrument of claim 19, wherein:
the one or more strain gauges are on an exterior surface of the beam; and
each cable from the plurality of cables extends exterior to the exterior surface of the beam between the proximal anchor and the distal anchor.

21. The surgical instrument of claim 19, wherein:
the surgical instrument further comprises a shaft, a plurality of drive members, and an end effector;
the shaft comprises a proximal end portion and a distal end portion;
the plurality of drive members is proximal of the proximal end portion of the shaft,
the end effector is distal of the distal anchor,
each cable of the plurality of cables is coupled to a corresponding unique drive member of the plurality of drive members; and
each cable of the plurality of cables is coupled to the end effector.

22. The surgical instrument of claim 19, wherein:
the surgical instrument further comprises a shaft;
the shaft comprises a proximal end portion and a distal end portion, with a longitudinal shaft center axis extending between the proximal end portion and the distal end portion;
the force sensor is located at least partially within the distal end portion of the shaft; and
the center axis of the force sensor is coaxial with the shaft center axis.

23. The surgical instrument of claim 19, wherein:
each cable of the plurality of cables is constrained to extend radially outwardly from the one or more strain gauges.

24. A surgical system comprising:
the surgical instrument of claim 19;
a manipulator unit to manipulate the surgical instrument operably coupled to the manipulator unit; and
a user console comprising one or more input devices to control movement of an end effector of the surgical instrument, wherein one or more forces measured by the force sensor are provided as feedback to a user via at least one of the one or more input devices of the user console.

* * * * *